United States Patent
Engel et al.

(10) Patent No.: US 11,626,190 B1
(45) Date of Patent: Apr. 11, 2023

(54) MOLECULAR TEST DATA SYSTEM WITH MAPPING ENGINE

(71) Applicant: Beacon Laboratory Benefits Solutions, Inc., Burlington, NC (US)

(72) Inventors: Louis Engel, Wake Forest, NC (US); George Harter, Raleigh, NC (US); Dawn Merolli, Burlington, NC (US); Rina Shah, Durham, NC (US)

(73) Assignee: Beacon Laboratory Benefit Solutions, Inc., Burlington, NC (US)

( * ) Notice: Subject to any disclaimer, the term of this patent is extended or adjusted under 35 U.S.C. 154(b) by 442 days.

(21) Appl. No.: 16/664,175

(22) Filed: Oct. 25, 2019

Related U.S. Application Data

(60) Provisional application No. 62/750,490, filed on Oct. 25, 2018.

(51) Int. Cl.
*G16H 10/40* (2018.01)
*G16B 40/00* (2019.01)
*G16H 15/00* (2018.01)

(52) U.S. Cl.
CPC ............. *G16H 10/40* (2018.01); *G16B 40/00* (2019.02); *G16H 15/00* (2018.01)

(58) Field of Classification Search
CPC ......... G16H 10/40; G16H 15/00; G16B 40/00
See application file for complete search history.

(56) References Cited

U.S. PATENT DOCUMENTS

| | | | | |
|---|---|---|---|---|
| 10,628,553 | B1* | 4/2020 | Murrish | G06F 16/2365 |
| 2002/0161606 | A1* | 10/2002 | Bennett | G16H 10/40 |
| | | | | 705/2 |
| 2002/0169766 | A1* | 11/2002 | Aoyama | G06F 16/10 |
| 2003/0204418 | A1* | 10/2003 | Ledley | G16H 40/20 |
| | | | | 705/3 |
| 2010/0017231 | A1* | 1/2010 | Galbraith | G16H 50/20 |
| | | | | 715/764 |
| 2013/0166315 | A1 | 6/2013 | Fonseca et al. | |
| 2013/0166593 | A1 | 6/2013 | Fonseca et al. | |
| 2013/0197943 | A1 | 8/2013 | Conlin et al. | |
| 2014/0019162 | A1* | 1/2014 | Skowronski | G16H 10/60 |
| | | | | 705/3 |
| 2016/0253461 | A1* | 9/2016 | Sohr | C25B 11/04 |
| | | | | 705/3 |
| 2016/0371446 | A1* | 12/2016 | Otin | G16H 40/63 |
| 2017/0300648 | A1* | 10/2017 | Charlap | G16B 20/00 |
| 2018/0189459 | A1* | 7/2018 | Diden | G06Q 10/1095 |
| 2018/0285391 | A1* | 10/2018 | Juneja | G06F 40/242 |
| 2019/0279777 | A1 | 9/2019 | Conlin et al. | |

* cited by examiner

*Primary Examiner* — Robert A Sorey
(74) *Attorney, Agent, or Firm* — Kilpatrick Townsend & Stockton LLP

(57) ABSTRACT

Features and aspects provide systems that advantageously enhance decisioning related to diagnostic testing by providing a mapping engine that interacts with disparate data processing systems to provide mappings of data elements from stored information for various types of diagnostic tests, including molecular tests. The mappings are stored in a decision support map file and can be referenced when molecular tests are ordered by diagnosticians to improve consistency, speed, and efficiency. Additionally, automated decisioning regarding review of molecular test orders can be provided by the system.

17 Claims, 5 Drawing Sheets

MOLECULAR TEST DATA SYSTEM WITH MAPPING ENGINE

CROSS-REFERENCE TO RELATED APPLICATION

This application claims priority from commonly-owned provisional patent application Ser. No. 62/750,490, filed Oct. 25, 2018, the entire disclosure of which is incorporated herein by reference.

TECHNICAL FIELD

This disclosure relates generally to data processing for diagnostic services and more particularly to a data processing system that produces a file or files to provide mappings of data elements from stored information for various types of tests. More specifically, the stored files facilitate identifying data elements across disparate systems in order to provide analytical support in connection with lab testing ordered by service providers, facilitating efficient interaction between and among data processing resources of various entities.

BACKGROUND

Diagnosticians often need to select lab tests. It is advantageous for diagnosticians to select the optimal test, or tests, for their subject in order for test specifications and results to be accessible and understandable to subjects, and relevant systems. As the number of labs, tests, third party computing systems, and data elements have increased, so has the amount of data related to testing, and thus the complexity of ordering, delivery, and fulfillment of diagnostic testing requests. Centralized data management systems are used to manage this complexity and provide decision support, data storage, and analytics.

SUMMARY

Features and aspects of the present disclosure provide systems that advantageously enhance decisioning related to lab testing by providing a mapping engine that interacts with multiple processing systems to provide mappings of data elements from stored information for various types of diagnostic tests, including molecular tests. The mappings can then be referenced when molecular tests are ordered by diagnosticians to improve consistency, speed, and efficiency, and to reduce errors caused by inconsistent data across disparate data processing systems.

In some examples, a processing device such as a microprocessor in a server receives a directory file from at least one of a number of lab computer systems. The directory file includes test identifiers, at least some of which correspond to molecular tests. The processing device parses the directory file to identify test data elements corresponding to each of the test identifiers and compares the test data elements for each of the test identifiers to decision support test data elements to produce a comparison result. The processing device then produces, based on the comparison result, mappings of test identifiers to decision support tests. The decision support tests are associated with the decision support test data elements and specified in a centralized test data management system. The decision support map, a data file including the mappings of test identifiers to decision support tests, is stored for reference to facilitate interaction between the lab computer systems and the centralized data management system, including interaction related to the molecular tests. When a test order is received from a diagnostic computing device, the decision support map can be accessed to determine a lab to be used to fulfill the test order by mapping the test order using the decision support map and specifying the manner in which the lab characterizes the test. The appropriate test order can optionally be sent electronically to the laboratory.

In some examples, the processing device receives identification data for a subject of a molecular test order. In some examples, the processing device receives a diagnostic code associated with the test order. In some examples, the processing device determines that a review of the test order is required. In some examples, the decision support map is produced by a mapping engine that applies auto-mapping rules that compare a lab computer test as defined by the test identifiers to the decision support tests set out in the centralized test data management system in existing decision support categories. The system can receive new decision support categories and selectively update the mappings based on the new decision support categories in response to input from an operator.

In some examples, the decision support map initially includes both definitive mappings and non-definitive mappings, and the definitive mappings and/or non-definitive mappings are displayed to an operator. The processing device receives input from the operator to convert the non-definitive mappings to definitive mappings or alter definitive mappings prior to storing the decision support map for use when tests are ordered.

These illustrative examples are mentioned not to limit or define the invention, but rather to provide examples to aid understanding thereof. Illustrative examples are discussed in the Detailed Description, which provides further description of various aspects and features of this disclosure.

DETAILED DESCRIPTION

Figure 1:
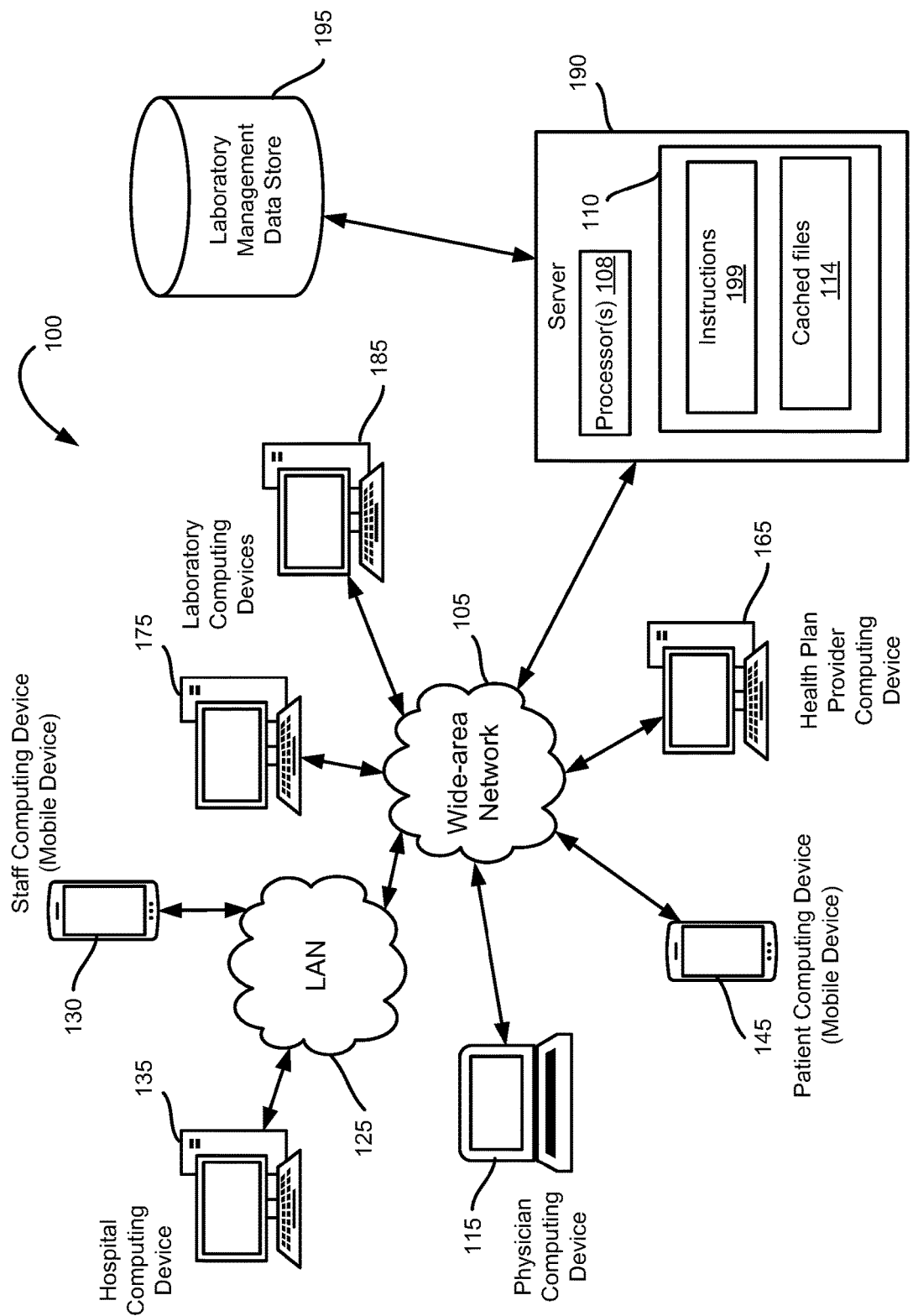
FIG. 1 is a system diagram depicting exemplary computing devices in an exemplary computing environment according to aspects of the disclosure.

Features and aspects of the disclosure are described herein in the context of a system for identifying, managing, and presenting information regarding medical tests ordered by health care providers, also referred to herein as diagnosticians. Features and aspects provide systems that advantageously enhance decisioning related to medical testing by providing a mapping engine that interacts with health care data processing systems to provide mappings of data elements from stored information for various types of medical tests. The mappings are stored in a decision support map file and can be referenced when tests are ordered by health care providers to improve consistency, speed, and efficiency. Additionally, automated decisioning regarding clinical review of test orders can be provided by the system. Such a clinical review may be required, for example, when a molecular test is ordered by a health care provider.

Patient information may include at least one datum from the data typically found on a patient's paper and/or electronic medical record, and/or a patient's paper and/or electronic health record relating to the patient's identification, physical characteristics, test results, medical conditions, medical history and/or care over time, and/or at least one datum related to a patient's current medical status or condition. A patient's medical history may include a longitudinal record of what has happened to the patient since birth. For example, a patient's medical history may include information relating to conditions, diseases, major and minor illnesses, surgeries, procedures, hospitalizations, medications, immunizations, and tests, as well as growth landmarks. The medical history may also include clinician assessments, for example a so-called SOAP (subjective, objective, assessment, and plan) including, for example, the chief complaint, history of the present illness, physical examination; assessment and plan. For purposes of this disclosure, a patient may also be referred to as a subject.

Laboratory information may include at least one datum from data relating to a laboratory, for example a laboratory offering diagnostic testing, information and services that patients and health care providers use to improve health care related decision-making by examining materials derived from the human body for the purpose of providing information on diagnosis, prognosis, prevention, or treatment of disease. The data relating to a laboratory may include, but is not limited to, data relating to test offerings, expertise, location, contact information, test processing time, sample collection, insurance reimbursement, insurance network coverage, as well as detailed information relating to specific tests and the relationship between published medical and/or scientific literature and a test or tests, and/or specific medical conditions. Data relating to laboratories may include a decision support map that further includes data describing mappings of test identifiers for a laboratory or laboratories to decision support tests. A laboratory may also be referred to as a lab.

Health plan information may include at least one datum from data relating to a health plan and/or a health insurance plan including, but not limited to, benefit information, coverage information, co-pay information, reimbursement information, claim information, claim processing time, test approval information, frequently asked questions, contact information and/or similar information relating to patient coverage. As used herein, health plan, health insurance and/or health insurance plan, are used interchangeably to refer to a type of insurance coverage that pays for medical, surgical and/or laboratory expenses incurred by the insured.

As used herein, health care provider (or diagnostician) refers to an individual or an institution that provides preventive, curative, promotional, or rehabilitative health care services to individuals, families or communities. An example of a health care provider includes, but is not limited to, a physician, a physician's assistant, a nurse, a nurse's aide, a pharmacist, a pharmacist's assistant, a dentist, a dentist's assistant, a dental hygienist, a laboratory technician, a physical therapist, an occupational therapist, a genetic counselor, and the like. As used in the present application, health care provider also includes administrative and other staff who may work with a health care provider.

As used herein a test identifier provides a unique index for a specific test within a specific laboratory. As used herein, test data elements include data elements corresponding to a test identifier that indicate characteristics of a test such as test name, panel name, billing code or codes and units billed. A decision support test is a test as broadly defined within a laboratory data management system. Such a test is broadly defined by stored data elements that can refer to a type of test that may be defined differently across individual laboratories. A decision support map in some aspects is a stored file that includes data describing mappings of test identifiers for a laboratory or laboratories to decision support tests. At least some of these test identifiers correspond to molecular tests.

As used herein laboratory includes, for example, a diagnostic laboratory that provides diagnostic testing, information and services that patients and health care providers use to improve health care related decision-making by examining materials derived from the human body for the purpose of providing information on diagnosis, prognosis, prevention, or treatment of disease. Examples of diagnostic tests are set forth below and include, but are not limited to, blood tests, including total cholesterol, Pap testing and white blood cell count, pathological testing, including biopsy analysis, and molecular and/or genetic testing that aid in the screening for, detection of and/or prognosis for and/or recovery from disease states.

In examples, a stored file or stored files may include laboratory information data. The stored file or stored files may include test data elements corresponding to a test identifier that indicate characteristics of a test such as test name, panel name, billing code or codes and units billed. A stored file or stored files may include decision support tests. A stored file or stored files may include a decision support map that further includes data describing mappings of test identifiers for a laboratory or laboratories to decision support tests. The file or files may be located on a single computing device or a multiple computing devices. A laboratory computing device can include laboratory information data and/or health plan information data. A health plan computing device can include health plan information data, patient information data and/or laboratory information. A health care provider computing device can include patient information data, health plan information data and/or laboratory information data. A health care provider computing device may also be referred to as a diagnostic computing device.

The process of producing mappings based the comparison of test data elements for each test identifier to data elements for decision support tests may include initially treating some mappings as definitive mappings, whereas some of the mappings produced above based the comparison of test data elements for each test identifier to data elements for decision support tests may be treated as non-definitive mappings. Non-definitive mappings may be presented to an operator and operator input can be received regarding the non-definitive mappings. The operator input includes definitive mappings of test identifiers to decision support tests for the mappings originally treated as non-definitive mappings. Non-definitive mappings can be converted to definitive mappings, which are then included in the decision support map or decision support maps stored to be referenced to determine what test is being ordered by a health care provider and which laboratory to use.

In some examples, when generating or referring to a decision support map, a laboratory data management system may receive laboratory information and/or health plan information. By way of a non-limiting example, a recommendation using the decision support map may present a health care provider with an option and/or options for a diagnostic test, a laboratory qualified to perform the diagnostic test and/or plan coverage information from a patient's health plan relating to coverage for the diagnostic test. Output may advantageously assist and/or support a health care provider's decision making.

Reference will be made in detail to implementations of examples as illustrated in the accompanying drawings. The same reference indicators will be used throughout the drawings and the following description to refer to the same or like items. These illustrative examples are given to introduce the reader to the general subject matter discussed herein. The following sections describe various additional non-limiting examples and examples of devices, systems, and methods for laboratory testing management using decision support maps.

In one example, a computing device that is part of a laboratory data management system, a system server, receives test directory files from laboratories. A laboratory data management system in the examples herein may also be referred to as a centralized test data management system, a laboratory benefits system, or a laboratory benefits management system, and is an example of a centralized test data management system. Such a system is typically operated by laboratory benefits organization, which may also be referred to as a laboratory management organization or a laboratory benefits service organization. Each directory file includes test identifiers used by a specific laboratory for multiple laboratory tests that can be ordered by a health care provider. At least some of these test identifiers correspond to molecular tests. The lab computer system used by a specific laboratory are these computer systems than operate on, send and receive, or store the directory file, which includes test identifiers specific to the specific laboratory. The server parses each directory file to identify test data elements corresponding to the test identifier for each test. The server can deal with multiple directory files from multiple lab computer systems. The server compares the test data elements for each test identifier to data elements for decision support tests used by the laboratory data management system and produces mappings of test identifiers to decision support tests based on the comparison. The server then produces and stores one or more decision support maps including the mappings of all test identifiers for all laboratories to decision support tests. Stored decision support maps can be referenced to determine what test is being ordered by a health care provider and which laboratory to use, as well as other necessary information such as the name and test identifier used by the selected laboratory for a given test.

Once decision support maps are resident in a data store accessible by the laboratory data management system, a health care provider can use a computing device to access a website or web service for retrieving patient information, laboratory information and/or health plan information. The health care provider can use the computing device to determine one or more possible laboratory tests through the website. For example, the health care provider can use the computing device to select or send medical information—such as one or more medical classification codes, symptoms, diseases, historical medical information for a patient, etc.—to the server. In response to receiving the medical information, the server can determine one or more possible laboratory tests. For example, the server may use the received medical information to query the data store including laboratory test categories and a decision support map to determine one or more possible laboratory tests and which test laboratories to use. The determined one or more possible laboratory tests can be based at least in part on the received medical information. At least one of the determined possible laboratory tests can be sent to the provider's computing device by the server.

In some examples, a health care provider can use the computing device to order one or more laboratory tests through a website or web service. For example, the server may send five possible laboratory tests to the computing device in response to receiving a list of symptoms from the computing device. In this example, a health care provider can select one or more of the possible laboratory tests and submit an order for the selected tests through the website. The test can then be mapped to a specific test identifier for a specific test laboratory using the decision support map. In one example, the server receives an order for one or more laboratory tests from the computing device and provides one or more additional and/or alternative laboratory tests. For example, a server may query a data store to determine an alternative laboratory test to recommend for an order for a particular laboratory test. An alternative laboratory test may be based on factors such as evidence-based guidelines, patient eligibility, historical medical information, and/or other factors. As another example, an additional laboratory test may be recommended if factors indicate that an additional laboratory test may need to be ordered. Thus, in one example, evidence-based guidelines may suggest that an additional laboratory tests should be ordered when a particular laboratory test is ordered. The additional laboratory test can also be mapped to a specific test identifier for a specific test laboratory using the decision support map. Numerous other examples are disclosed herein, and variations are within the scope of this disclosure.

FIG. 1 is a system 100 diagram depicting exemplary computing devices in an exemplary computing environment according to one example. The system 100 shown in FIG. 1 includes a wide-area network 105 in communication with various devices associated with health care providers or consumers, e.g. doctor offices, hospitals, patients, field representatives, which may include health care provider customer representatives, laboratory customer representatives, and/or health plan customer representatives, health plan providers, internal labs, and external labs. The wide-area network may be implemented by secured connections over the public Internet. The various computing devices that are connected to network 105 in this example include, mobile computing device 130, which may be used by a hospital staff member, and mobile computing device 145, which may be used by a patient.

Still referring to FIG. 1, the various computing devices also include hospital desktop computer 135, lab desktop computers 175 and 185, a physician's notebook computer 115, and a desktop computer 165, which may be used by a health plan providers personnel. The network 105 in FIG. 1 is also in communication with a server 190 and the server 190 is in communication with a laboratory management data store 195. The network 105 may be in communication with other networks such as, for example, local area network (LAN) 125, which is associated with a hospital and is provides a connection to mobile computing devices 130 and 135. In this example, one of the desktop computers 175 and 185 may be used by a testing laboratory that is internal to the laboratory management system entity and the other may be used be an external testing laboratory. Lab desktop computers 175 and 185 are examples of lab computing devices that are part of or connected to a laboratory computer system.

The computing networks shown in the example of FIG. 1 may use any combination of wired and/or wireless communication links, and may include two or more networks. Any number of computing devices may be associated with the networks. Numerous other networks associated with entities such as doctor's offices, health plan providers, patients, or laboratories may be present. Communication between devices, networks, or entities, or some combination thereof, may be facilitated by the Internet. For example, network 105 may be in communication with network 125 through the Internet. In some examples, such communication may be secure. For example, a hypertext transfer protocol secure (HTTPS) may be used to provide encrypted communication between various devices, networks, or entities, or some combination thereof. Communications between two or more systems or devices can also be achieved by using secure sockets layer ("SSL") or transport layer security ("TLS"). In another example, a virtual private connection (VPN) may be used to provide communication. For example, a gateway (not shown) associated with network 125 can be in communication with a gateway (not shown) associated with network 105 through a VPN connection. In one example, a VPN connection may contain a single tunnel connection. To at least provide redundancy, however, a VPN connection may include two or more tunnel connections. Thus, if one tunnel connection in the VPN connection fails, communication may still be successful through the other tunnel connection.

The server 190 shown in FIG. 1 may be any computing device capable of communicating with a network, such as network 105, and capable of sending and receiving information to and from another device. For example, in the example shown in FIG. 1, the server 190 may receive a request from various devices such as mobile computing device 130, desktop computer 135, or other devices. In this example, the server 190 may respond to the request by sending information back to the requesting device through the network 105. Thus, if server 190 receives a request from notebook computer 115 associated with a doctor office through network 105, then the server 190 may process the request including performing any necessary communication with any other device and respond to the request by sending a response back to the notebook computer 115 through the network 105. In an example, the server 190 can communicate with a gateway (not shown) associated with the server and network 105. The server 190 may be in communication with one or more data stores, such as laboratory management data store 195.

Continuing with FIG. 1, server 190 may be in communication with one or more additional servers (not shown). In some examples, server 190 may communicate with one or more additional devices to process a request received from another device. For example, the server 190 in FIG. 1 may be in communication with an additional servers, at least one of which may be used to process at least a portion of a request received from another device, such as mobile computing device 130, or desktop computer 175. In other examples, the server 190 may send a request to one or more devices and process any response received from the device or devices. For example, server 190 may send a request to desktop computer 135 associated with a hospital. In this example, the server 190 may receive a response from the desktop computer 135 and process the response. For example, the server 190 may store information related to the response in data store 195. The data store 195 can include numerous separate data stores, data tables, databases, or other data storage mechanisms and media for storing data relating to particular aspects of one or more of the examples disclosed herein.

Server 190 of FIG. 1 further includes a processor or processors 108 and a non-transitory memory device 110. Memory device 110 is a non-transitory computer-readable medium used to store computer program code instructions 199 for causing processor 108 to perform operations for receiving a directory file from laboratory computer system. The computer program instructions are executed by the server to parse the directory file to identify test data elements corresponding to the test identifier for each test and compare the test data elements for each test identifier to data elements for decision support tests used for laboratory management by the centralized test data management system that includes server 190. Computer program code instructions 199 include a mapping engine with auto-mapping rules that compare each lab's tests to the rules to determine how to map the laboratory's test to a decision support test and to ultimately generate one or more decision support maps. These decision support tests can be organized into decision support categories to making mapping more efficient. At least some of the tests being mapped include molecular tests. Since information regarding a laboratory's test is stored in a lab computer system, these tests may also be referred to herein as lab computer tests. A decision support map is used when tests are selected by diagnosticians. Non-transitory memory device 110 may also include cached files 114, such as portions of directory files or intermediate data stored and used by the processor to perform these operations. The server 190 may include adapters, routers, etc., for accessing network-attached data stores, a communications network such as wide-area network 105, or both.

Figure 2:
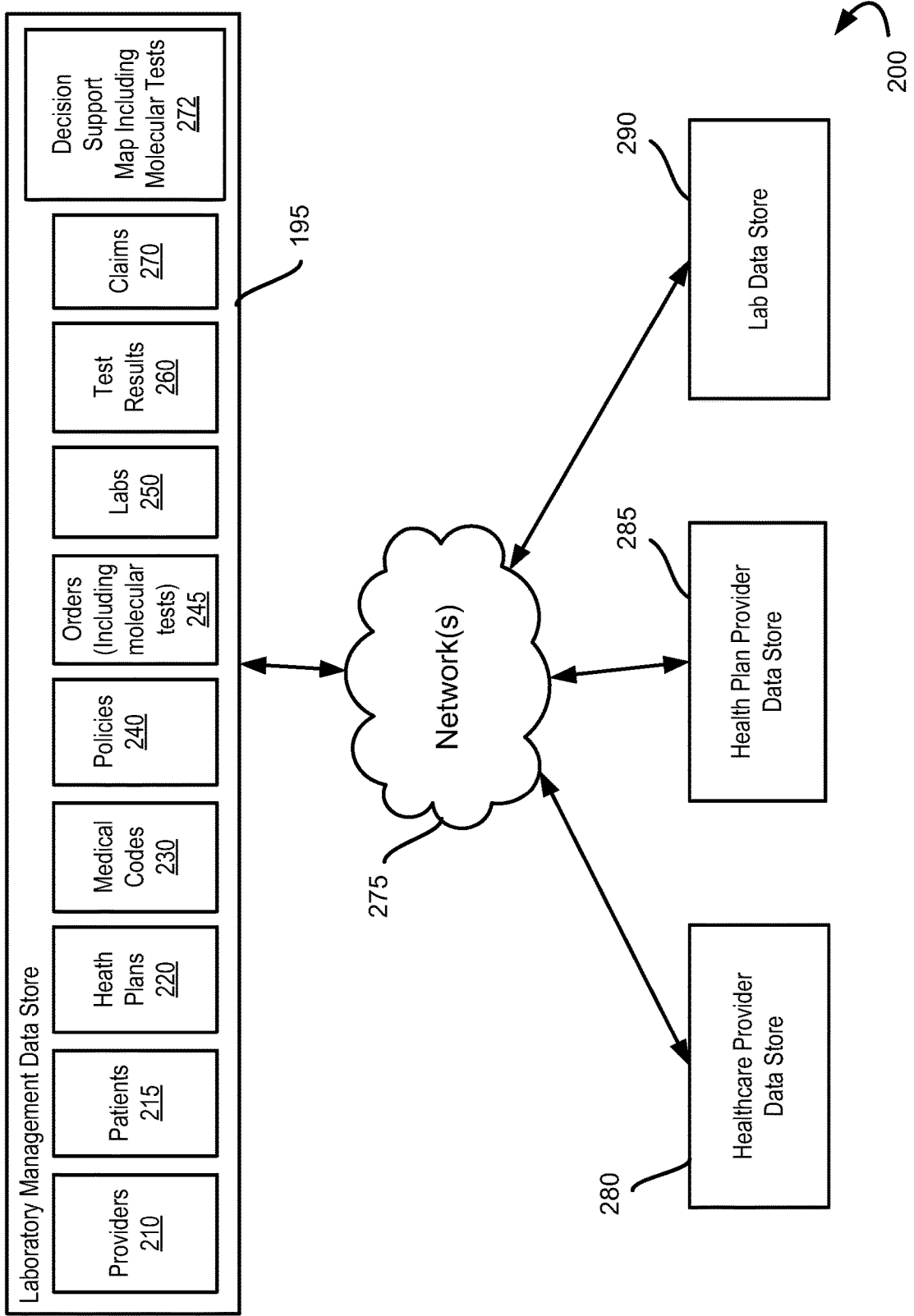
FIG. 2 is a diagram illustrating an example of a system of various data stores connected with each other and the various computing devices shown in FIG. 1 according to aspects of the disclosure.

FIG. 2 is a diagram illustrating an example of a system 200 including the various data stores that can store information according to some examples. In the system 200 shown in FIG. 2, the laboratory management data store 195, a health care provider data store 280, a health plan provider data store 285, and a laboratory data store 290 are in communication with each other through network 275. Network 275 can include network 105 and/or network 125 as shown in FIG. 1. Information stored in a data store may be accessed by one or more other data stores. For example, information stored in the health plan provider data store 285 may be accessed by the laboratory management data store 195. Information stored in the laboratory management data store 195 may be accessed by the health plan provider data store 285. Information may be sent to or saved by, or both, one or more data stores from another data store. For example, information regarding a laboratory testing order may be sent by the health care provider data store 280 through network 275 to the laboratory management data store 195. In this example, the laboratory management data store 195 may store laboratory testing order data to an orders database 245. The testing order data includes data on orders for molecular tests. In another example, information regarding the results of a laboratory test may be sent from laboratory management data store 195 to health care provider data store 280.

In the example shown in FIGS. 1 and 2, the laboratory management data store 195 includes information related to various aspects of a laboratory data management system. The laboratory management data store 195 includes provider information 210 related to health care providers. For example, provider information 210 can include names, addresses, phone numbers, personnel, usernames, passwords, other security information, access levels, and other information associated with one or more providers. The laboratory management data store 195 in FIG. 2 contains patient information 215 patients. Information related to patients may include patient names, addresses, telephone numbers, providers with which the patients are associated, medical history, medications, relatives, health care provider plans, account balances, access information, or other information related to one or more patients.

In FIG. 2, the laboratory management data store 195 includes health plan database 220 related to health plan providers. For example, information related to health plan providers can include insurance companies, various insurance plans, payment information for laboratory tests, information related to one or more patients, deductible information, testing notification data, or other information associated with one or more health plan providers. The laboratory management data store 195 in FIG. 2 include medical code database 230 including information related to medical codes used to designate tests and procedures. Such information may include medical classifications for diseases, signs, symptoms, potential causes of injury, potential causes of one or more diseases, testing procedures, laboratory tests, other coding information, or a combination thereof In one example, medical code information can include data from the International Statistical Classification of Diseases and Related Health Problems (ICD) such as the ICD-9 medical classification list or the ICD-10medical classification list or future versions of ICD or other codes. Such codes may be referred to herein as medical or diagnosis codes. In another example, information related to medical codes 230 may include data such as the American Medical Association's (AMA) CPT data code files that provide at least a list of CPT procedural codes.

The laboratory management data store 195 in FIG. 2 contains a policy database 240. A policy may include evidence-based guidelines for one or more diseases, illnesses, medical tests, etc. In one example, policy information stored in database 240 includes information that may be used to offer suggestions regarding tests or procedures that are typically followed for a particular illness, system or set of symptoms, or other evidence-based information. In one example, a set of questions related to one or more policies, illnesses or one or more symptoms may be stored in database 240. The laboratory management data store 195 in FIG. 2 includes order information database 245. For example, information related to orders can include information related to health care providers that have placed an order, information related to patients for which an order has been placed, information related to the tests that have been performed, billing information, payment information, accounts receivable information, order status, one or more laboratories associated with orders, test results, or a combination thereof The laboratory management data store 195 in FIG. 2 includes laboratory information database 250. For example, laboratory information database 250 may contain information such as location, costs for various tests, turnaround time, type of tests performed, current capacity levels, historical information related to tests that have been performed by one or more laboratories, current information regarding one or more orders such as order statuses, addresses, personnel, contacts, usernames, passwords, other identification, or other laboratory information. The laboratory information database 250 may contain information to distinguish internal laboratories from external laboratories. Internal laboratories can include laboratories owned by or affiliated with one or more organizations operating a laboratory benefits management system. For example, if an organization is operating the laboratory benefits management system described herein and the organization owns a laboratory, in one example, the laboratory can be considered an internal laboratory. Examples of external laboratories can include laboratories not owned or operated by an organization operating the laboratory benefits management system. For example, in one example, an organization may own several laboratories, but none of the internal laboratories perform a particular test that has been ordered. In this example, the laboratory information database 250 may contain information for an external laboratory that has the capability to perform the test. Numerous other examples or additional information that may be stored in the laboratory information database 250 will be obvious to one of skill in the art.

The laboratory management data store 195 in FIG. 2 contains laboratory test results database 260. Information related to laboratory test results can include information such as the actual results of the test, suggested follow-up tests, historical information based on past test results, diagnostic information, information related to medical guidelines or thresholds for one or more tests, and other information related to test results. The laboratory management data store 195 in FIG. 2 includes claims database 270. For example, information related to claims can include the payment status for claims, whether the claim has been submitted to a health plan provider, eligibility verification information, benefits determination information, whether a claim requires editing, whether the claim needs or has been adjusted, or other information related to one or more claims.

The laboratory management data store 195 in FIG. 2 contains at least one decision support map 272, which provides mappings of laboratory tests to decision support tests, including mappings for molecular tests. A typical laboratory management data store 195 may contain multiple decision support maps. A decision support map is a stored file that includes data describing mappings of test identifiers for a laboratory or laboratories to decision support tests. Laboratory tests ordered within the laboratory data management system can be mapped to specific test identifiers for specific test laboratories using the decision support maps.

In some examples, data store 195 may access or store information, or both, in one or more data stores, such as data store 280, data store 285, or data store 290. For example, in one example, data store 290 may contain laboratory test results 260. In this example, data store 195 may be able to access information or store information stored in laboratory test results database 260 by accessing data store 290 through network 275. One or more data stores may be associated with any number of entities. For example, data store 280 may be associated with a health care provider such as a hospital or a doctor's office. In one example, data store 280 may be associated with a hospital and one or more satellite branches such as other facilities located in surrounding communities. In other examples, data store 280 may be associated with multiple hospitals or other facilities owned, affiliated with, or related to one another. Data store 285 may be associated with a health plan provider such as an insurance company. Data store 290 may be associated with one or more labs such as an internal laboratory or an external laboratory.

The laboratory data management system can include a web portal. The web portal may be horizontal or vertical, or a combination of a horizontal portal and a vertical portal. A health care provider may access patient information, health plan information and/or laboratory information through the portal. In an example, a health care provider may be presented with a single web page that brings together and/or aggregates content from other systems and/or servers, and/or a database, or databases, that include patient information, health plan information and/or laboratory information. A web portal may also be configured to provide functionality described herein by providing an interface for a laboratory to upload its directory file of laboratory tests offered. In this example, the web portal may be hosted on a portal server (not shown) that includes connectivity to an application server.

By way of example, Service-Oriented Architecture (SOA) is one example of how a portal can be used to deliver application server content and functionality. The application server or architecture performs the actual functions of the application. This application server is in turn connected to database servers, and may be part of a clustered server environment. High-capacity portal configurations may include load balancing equipment. SOAP, an XML-based protocol, may be used for servers to communicate within this architecture. The server hosting the portal may only be a "pass through" for the user. By use of portlets, application functionality can be presented in any number of portal pages. For the most part, this architecture is transparent to a user.

Figure 3:
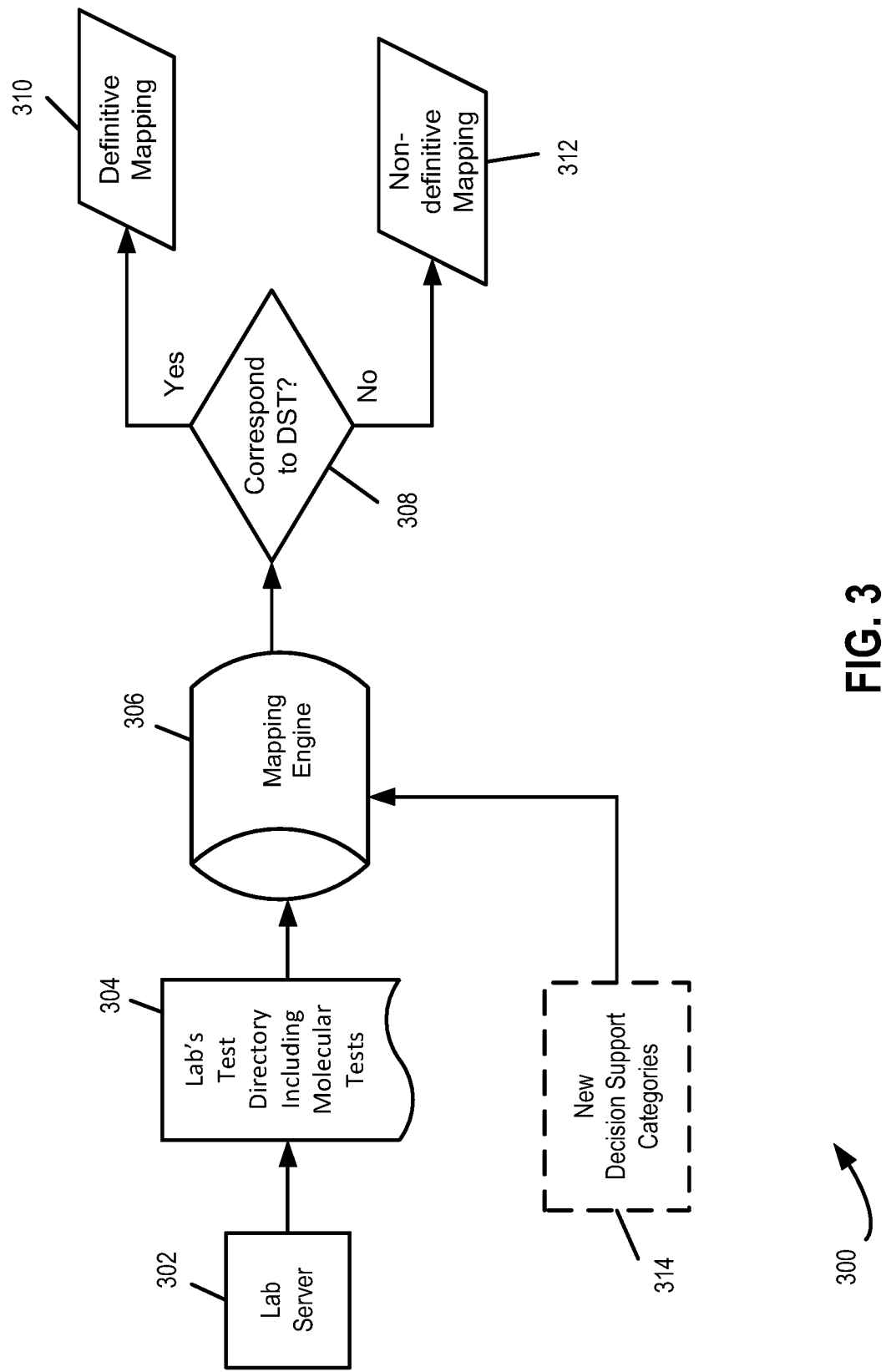
FIG. 3 is a block diagram illustrating an example of a software architecture providing test mapping according to aspects of the disclosure.

Mapping of test identifiers, including identifiers for molecular tests, according to some aspects can be accomplished by a software utility that includes an upload feature and a mapping engine. The architecture 300 of this utility is shown in FIG. 3. To use the utility, a lab server 302 uploads the lab's test directory 304, which includes test identifiers and data elements for molecular tests. A molecular test a laboratory test that checks for certain genes, proteins, or other molecules in a sample of tissue, blood, or other body fluid. Molecular tests can also check for certain changes in a gene or chromosome that may cause or affect the chance of developing a specific disease or disorder, such as cancer. The text directory can be provided in any suitable format, for example, a delimited text file or a spreadsheet. In this example, the test directory includes a test identifier and data elements that identify the test that corresponds to the test identifier. The data elements may include a test/panel name, billing codes and units billed. Optionally, the laboratory data management systems' server can identify any billing code that is not currently valid or has been formatted incorrectly, and notify the laboratory of the error through a user interface or web portal, which may be accessed using computing device 175 or computing device 185. For many errors, the laboratory can correct the data in the file and initiate an upload again.

In FIG. 3, each test in a test directory is compared to decision support test by mapping engine 306. Mapping engine 306 includes mapping rules that compare each lab computer system test to tests within decision support categories set out in the laboratory data management system to determine if the test maps to a decision support test (DST). These decision support categories include molecular test decision support categories. Mapping engine 306 can be implemented with computer program code instructions 199 of FIG. 1. Some mappings produced based on the comparison of test data elements for each test identifier to data elements for decision support tests by decisioning software module 308 may be treated as definitive mappings 310, whereas some of the mappings produced by decisioning software module 308 may be treated as non-definitive mappings 312. Decisioning software module 308 can also be implemented as part of computer program code instructions 199 of FIG. 1. Non-definitive mappings may be presented to an operator and operator input can be received regarding the non-definitive mappings. The presentation to the operator may include mappings to decision support categories to narrow the selection and speed the process. The operator input includes definitive mappings of test identifiers to decision support tests for the mappings originally treated as non-definitive mappings by the processing device 108 running decisioning software module 308. Some examples for determination rules that can be employed by mapping engine 306 include mapping by billing code alone, mapping by test name alone, and mapping by both billing code and test name.

Mapping can be determined by billing code alone. For example, a DST for cystic fibrosis sequencing may have an identifier in the laboratory data management system of "10147." If a laboratory normally bills a cystic fibrosis sequencing test by CPT alone, for example, CPT 81223, and it is known within the mapping engine that these two tests are an exact match, the system will map this test by the laboratory to DST identifier 10147. One might call this match condition a "green" match condition for a definitive mapping. If the laboratory's test fails in terms of the system including a rule for an exact match to the CPT code, but a match is known for a portion of the test name, such as "cystic fibrosis," then the laboratory's test is handled as a non-definitive mapping, or as an example, might be considered to have a "yellow" match condition, in which case this test is flagged for manual intervention, so that the mapping is ultimately presented to an operator for confirmation or correction. An operator can then provide input to indicate the appropriate DST. It should be noted that the term "operator" is used herein to denote personnel affiliated with the laboratory data management system, as distinct from "users" who may be affiliated with a medical provider or laboratory making use of the laboratory data management system.

As another example, mapping can be determined by test name alone. DSTs in this category are matched based on the test name. For example, EndoPredict® breast cancer test is a DST that is defined by name only since different codes can be used to bill the test, however the name is very specific. The mapping engine 306 of FIG. 3 will evaluate the test name in the laboratory's test directory. If the lab's test name is an exact match, it might be termed as having a "green" match condition for a definitive mapping. Otherwise, a non-definitive mapping can be termed a "yellow" match condition and again referred for operator input.

Mapping can, as another example, be determined by both name and billing code. DSTs in this category are evaluated by billing code(s) and the name of the test together. For example, a test such as a dermatopathology test can evaluated by CPT(s) and test name. The rule evaluates the laboratory's tests, with a "green" match condition for definitive mapping being indicative of an exact match. A partial match would again be termed a non-definitive or "yellow" match condition mapping and again be referred for manual input. A status display (not shown) can display indicators in green and yellow to indicate these conditions to a user.

In setting up the rules for the mapping engine 306 of FIG. 3, each DST can have its own set of green and yellow condition matching rules. Each DST is also evaluated to ensure that these rules do not overlap or result in erroneous mapping. The more green match conditions that occur during mapping, the less manual intervention is required. Thus, more carefully designed rules result in more efficient onboarding of tests from a given laboratory. Rules can also be periodically updated, and various billing codes can be used. For example, McKesson codes, ez codes, or z codes can be used in addition to or instead of CPT codes.

Mapping engine 306 can periodically, or on demand, receive new decision support categories 314 that are added to the laboratory data management system. These new decision support categories may replace existing decision support categories. The mappings 310 and 312 can be selectively updated based on the new decision support categories in response to input from an operator. As new decision support categories are added to the laboratory data management system, mapping engine 306 as implemented with computer program code instructions 199 of FIG. 1 can re-evaluate every previously mapped test, offered by each lab. The re-mapping algorithm may be activated or bypassed at the direction of an operator that is authorized according to authorized user types. The output of the application of this aspect of computer program code instructions 199 is that new business rules are applied in a discretionary manner.

Figure 4:
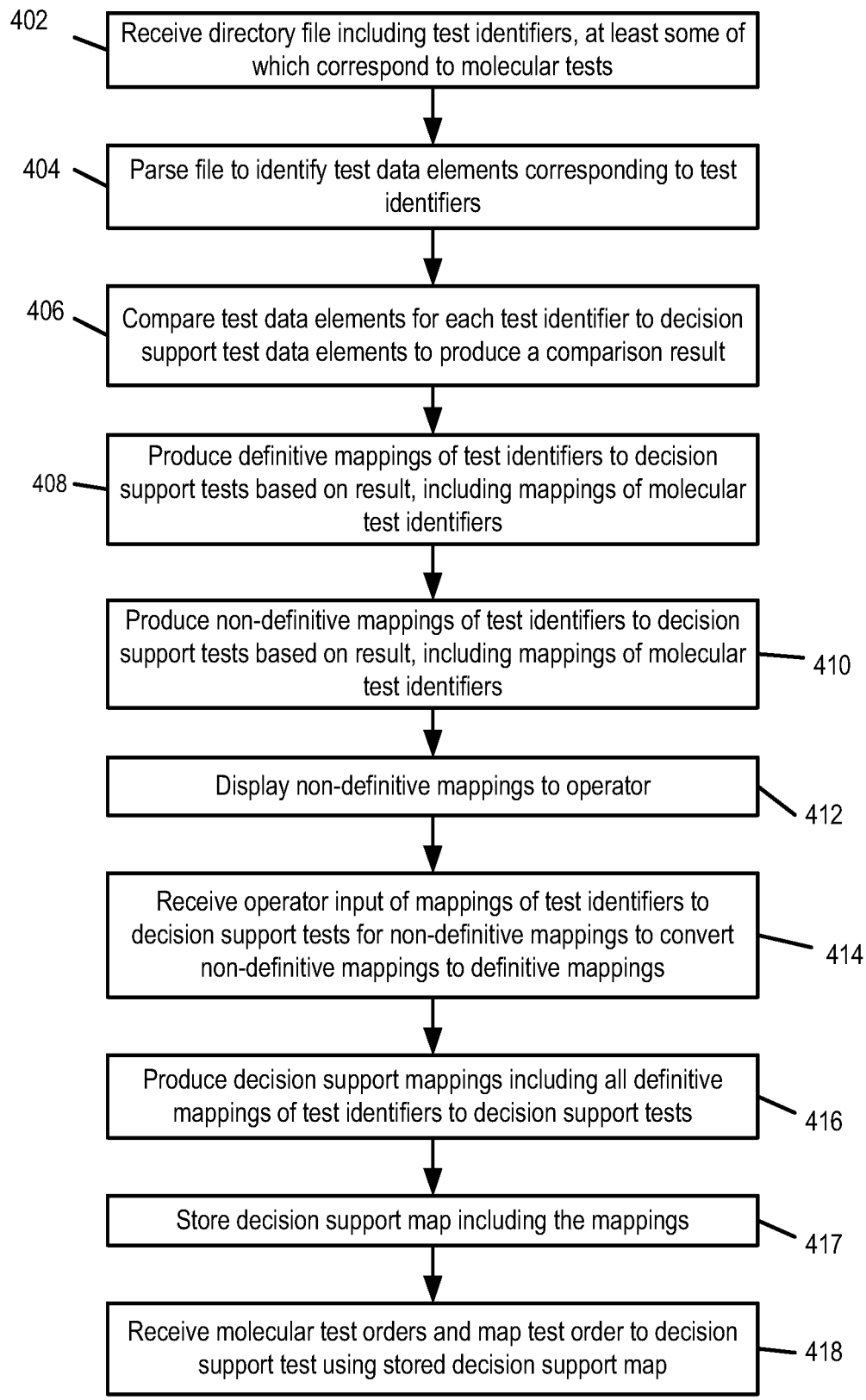
FIG. 4 is a flowchart of an example of a method for providing test mapping according to aspects of the disclosure.

FIG. 4 is a flowchart illustrating a method 400 for carrying out the mapping as described above. Method 400 will be described with respect to FIG. 1, FIG. 2, and FIG. 3 in addition to FIG. 4. At block 402 of FIG. 4, a processing device such as processor 108 of FIG. 1 receives a directory file including test identifiers, at least some of which correspond to molecular tests. At block 404, the processing device parses the directory file to identify test data elements corresponding to test identifiers. At block 406, the processing device compares test data elements for each test identifier to decision support test data elements, which may be accessed in one of the data stores such as data store 195. The processing device produces a comparison result. At block 408, definitive mappings of test identifiers to decision support tests are produced, to the extent that definitive mappings can be made. These mappings include mappings of molecular test identifiers. At block 410, non-definitive mappings are flagged. These non-definitive mappings may also include mappings of molecular test identifiers. At block 412, the non-definitive mappings are displayed to an operator. At block 414, the processing device receives operator input of mappings of test identifiers to decision support tests for non-definitive mappings to convert non-definitive mappings to definitive mappings. In some aspects, the system can also present definitive mappings for verification. At block 416, decision support mappings including all mappings of test identifiers to decision support tests are produced. At block 417, a decision support map including the mappings is stored. As an example, the decision support map 272 can be stored in data store 195 as shown in FIG. 2. Test orders, including molecular test orders, are received and can be mapped by reference to the decision support map in order to determine a test to order as shown at block 418. This use of the decision support map can, for example, provide advanced decision support as discussed with respect to FIG. 5.

The decision support map can be referenced as part of determining a test to be administered when a subject visits a health care provider. For example, the subject may visit a health care provider physician at a doctor's office. Once the subject visits the health care provider, the health care provider reviews patient information, and may input additional patient information, for example in conjunction with an examination of the subject the provider may input information using computing device 115 of FIG. 1. For example, the physician at the doctor's office may determine the subject's current symptoms and medical history. The physician could access the system through a web portal on computing device 115. The physician could access patient information through the web portal and could also access health plan information and/or laboratory information. The physician, and/or another health care provider, may also input new patient information, including the patient's medical condition through the web portal. The patient information, including updated patient information, health plan information and laboratory information are received and/or accessed.

Test labs may be selected on any number of criteria, including but not limited to, health plan benefit information, laboratory expertise with a test or tests, lab processing time, laboratory fee information, and similar information used by health care providers and/or health plan providers to select a laboratory for diagnostic testing. These laboratories have had their tests mapped to decision support tests as designated in the laboratory data management system.

In some examples, information may be received that contains one or more tests for one or more patients to be ordered. In another example, information may contain present or historical, or both, information related to one or more patients and this information may be used in processing with reference to a policy or policies to determine one or more recommended tests. The decision support map may also be referenced to determine one or more recommended tests. Information can include current and/or past medical statistics, current and/or past biographical information, current and/or past laboratory orders, current and/or past laboratory results, current and/or past symptoms, current and/or past diagnoses, current and/or past treatments, current and/or past prescriptions, current and/or past indications, current and/or past health care providers, current and/or past insurance providers, medical codes, other medical information, or a combination thereof.

The processing of testing information may occur through a decision support component. Physician decision support may present a physician with options, for example options for laboratory tests for a patient, based on patient information, health plan information and/or laboratory information and physician decision support may use the decision support map to present these options. For example, if processing patient information suggests an illness, frequently ordered laboratory tests for that illness may be presented. If the information includes information relating to one or more lab tests and/or lab test results, processing may result in presenting additional laboratory tests. The one or more additional laboratory tests can be presented on the received patient information, health plan information and/or laboratory information, medical information for a patient, past medical information for a patient, medical information for a population of patients, evidenced-based medical guidelines, information corresponding to one or more laboratories, information corresponding to one or more health care providers, information corresponding to one or more insurance providers, information corresponding to one or more laboratory system management providers, other medical information, or a combination thereof. In one example, if the information includes an order for one or more laboratory tests, processing may result in the presentation of one or more alternative laboratory tests making references to the decision support map to identify and distinguish these alternative laboratory tests.

Information provided, and/or decision support information, may be accessed, collected, and/or verified. For example, information contained in a request may be verified against one or more medical classification lists such as ICD-9, ICD-10, or CPT data. In one example, a policy including evidence-based guidelines may be used to determine one or more laboratory tests —including, but not limited to, additional and/or alternative laboratory tests if the received information includes an order for one or more laboratory tests—for one or more patients associated with the received information. For example, information related to a patient's medical history may be accessed and used to determine whether one or more additional or alternative tests for the patient may be presented based at least in part on one or more evidence-based guidelines. Similarly, information related to a patient's symptoms may be contained in the information or otherwise accessed and used to determine whether one or more laboratory tests for the patient or patients can be recommended based at least in part on one or more evidence-based guidelines. In some examples, a patient's medical history, past symptoms, present symptoms, or a combination thereof, may be used to determine one or more laboratory tests, optionally making reference to the decision support map. For example, received information may include a patient's current symptoms, which are used to determine one or more suggested laboratory tests for the patient. In one example, information includes symptoms as well as a laboratory test for a patient and the symptoms are used, at least in part, to determine one or more additional or alternative tests for the patient. Other information, such as a patient's medical history, may be used in connection with a patient's symptoms to determine one or more tests to be presented.

The laboratory data management system may include processing of laboratory information, health plan information and/or patient information to develop an option or options for a laboratory or laboratories to perform a test, e.g. a test requested by a health care provider and/or a test presented to a health care provider though the processing described herein with reference to a policy or policies, making use of the decision support map to identify a laboratory and an equivalent test. In an example, processing may present options for one or more laboratories to perform at least a portion of a test. Such a determination may be based on any number of factors. For example, a determination may be based on a timeframe for completing at least a portion of the order. In this example, a laboratory that has the capacity to provide laboratory results for the portion of the order may be selected. For example, if an order specifies a particular laboratory test and ten laboratories are available to complete the laboratory test, then the laboratory with the overall lowest cost for performing the laboratory test may be chosen. A determination can be based on other factors such as location of the laboratory, whether the laboratory is an in-network or out-of-network laboratory, whether the laboratory is owned or operated by the laboratory benefits organization, or other factors.

Processing may also include processing laboratory information including status of an order; laboratory results; laboratory reimbursement; and/or other items of interest to a health care provider, patient, health plan provider and/or laboratory. Information on these, or similar, items may be presented to a health care provider for review. For example, if an external laboratory is selected to perform a laboratory test, the status of the laboratory test may be tracked, possibly as a decision support test using the decision support map. The status of the laboratory test may include information such as whether a sample related to the test has been collected, the historical location of the sample, a current location of the sample, whether the laboratory test has been started, an expected completion date for the laboratory test, whether the results of a laboratory test are available, whether the results of a laboratory test have been received, or other status information. In some examples, status information may be exchanged between various devices. For example, referring to FIG. 1, an internal laboratory may send status information to server 190 through network 105, which is stored in data store 195. In one example, status information may be sent from server 190 to an external laboratory through network 105.

The processing of laboratory information may include verification of a test. A test verification may be based on one or more medical classification lists. For example, a laboratory test requested for a patient based as a decision support test may be verified against an ICD-9 or ICD-10 medical classification list. In an example, the request contains a code that represents a laboratory test to be performed for a patient. A request may contain a name of a laboratory test to be performed. In this example, a code—such as an ICD-9, ICD-10, or CPT code—may be assigned for the laboratory test to be performed by a given laboratory based at least in part on the mappings within the decision support map. In one example, the test may be a molecular test. As with other tests, the molecular test may be mapped to particular labs and codes for those labs using the decision support map.

In an example, a determination as to whether present one or more laboratory tests may be made on patient information, including current symptoms of a patient. Patient information received by server 190 may include a list of current and/or past symptoms for a patient. In one example, server 190 accesses data store 195 including a policy or policies to determine if there are any tests that are recommended based on the symptoms. In some examples, patient information including historical medical information for the patient is also used to determine which tests, if any, are recommended. For example, if a patient has a history of having a bladder infection and symptoms for the patient provided in the patient information suggest a bladder infection, among other potential illnesses, then one or more laboratory tests related to a bladder infection may be presented. In some examples, patient information includes laboratory test data. In this example, server 190 may access a policy or policies stored in data store 195 to determine whether one or more additional tests are presented based at least in part on the requested laboratory test as well as the patient's symptoms. The foregoing are illustrative examples of the use of a decision support map to present laboratory tests for patients. As discussed herein, patient information may include current symptoms, medical history, past symptoms, laboratory test performed, and the results and a variety of other information set forth above.

As noted herein, a policy, e.g. a policy including evidenced based guidelines; symptoms, historical medical information, illnesses or diseases, any laboratory tests, or a combination thereof, may be used to determine one or more tests to present to a health care provider or other user of the system. One or more data stores may be queried in making such a determination. In one example, information is contained in a single data store. For example, in FIGS. 1 and 2, data store 195 may contain historical medical information for a patient and evidence-based guidelines that are used, along with information received in the request, to determine whether one or more tests are recommended. In another example, information is contained in two or more data stores. For example, referring to FIG. 2, data store 195 may contain medical codes, data store 280 may contain evidence-based guidelines for the health care provider, and data store 285 may contain historical information for patients. In this example, server 190 may receive a request for a laboratory test and a list of symptoms for a patient. In determining whether one or more tests are recommended, server 190 may access data store 195 for one or more medical codes related to the requested laboratory test, data store 280 for evidence-based guidelines based on the list of symptoms for the patient provided in the request or the requested laboratory test, or both, and data store 285 for historical information related to the patient.

If one or more tests are available, then laboratory options are presented to a health care provider. In some examples, information presented relating to a laboratory test may include, but is not limited to, one or more classification codes for the laboratory test, a name for the laboratory test, one or more reasons as to why the laboratory test is recommended, medical information related to the recommended laboratory test and a patient for which the laboratory test is recommended, statistics related to the laboratory test, information regarding evidence based guidelines that were used to make the recommendation, one or more medical references regarding the recommendation, other medical information, or a combination thereof. Specific information regarding a laboratory to be used and its name and/or codes for the test may be presented by looking up the mapping for the test in the decision support map. In some aspects, information presented may be customized. For example, a health care provider may specify that a list of tests and/or laboratories should be presented. A physician in doctor's office, however, may specify that a list of laboratory tests as well as the criteria, for example the policy, used to determine the laboratory tests should be provided.

Health plan information may be utilized to present patient benefit information relating to one or more laboratory tests, and/or with respect to one or more laboratories. Health plan benefit information, laboratory information and/or laboratory test information may be processed and/or presented in any number of ways. In an example, information is received from a website associated with a laboratory benefits organization, a health care provider, or a third-party. Information may be transmitted and exchanged in any number of languages or in any number of formats including, but not limited to, ActionScript®, AJAX, ASP, C, C++, HTML, JAVA JavaScript, JSON, JSP, MXML, PHP, XML, or XSLT. In examples, information may be received from one or more data stores. For example, information may be received from a data store associated with a health care provider. Information may be in an archive or compressed format, or both, such as JAR, ZIP, RAR, ISO, or TAR. A combination of protocols, languages, formats, and/or devices may be used to send or receive a response according to various aspects.

After information is presented to a health care provider, the provider may select one or more tests to be run. In one example, after selection, a notification may be provided to one or more users of the laboratory data management system. For example, if a nurse originally submits an order for a physician, then the nurse or the physician, or both, may receive a notification that the order has been approved. Where a request contains tests for multiple patients associated with multiple physicians, then each physician may receive a notification associated with his or her patients. For example, a request may contain a laboratory test request for patient A associated with physician A, a laboratory test request for patient B associated with physician A, and a laboratory test request for patient C associated with physician B. In this example, physician A may receive one notification for the laboratory test request associated with patient A and another notification for the laboratory test request associated with patient B. Alternatively, physician A may receive a single, combined notification for the laboratory test requests associated with patient A and patient B. In addition, physician B may receive a notification for the laboratory test request associated with patient C. The tests requested may be mapped using a decision support map as described herein.

In addition to connecting various parties in a health care environment, by requiring that the health care provider, laboratory, genetic counselor, patient, health plan, and testing laboratory complete certain steps during the process, the decision support map can be used to control the workflow. For example, a physician may suggest a particular test. A genetic counselor may then examine the request to ensure it is the appropriate test to apply. The request may then be evaluated by the system to determine if the patient is eligible to receive health plan benefits to pay or help pay for the test. Once each step is complete, then the patient can be authorized for the test and then decide whether or not to have the test administered.

As noted herein, the information presented may include information relating to laboratory where a test may be performed. The selection of laboratories to be presented may be made based on laboratory information from one or more laboratories as supplied in directory files and stored as part of a decision support map. In one example, one or more labs are presented based on the test or tests to be presented as mapped in a decision support map. For example, a first test and a second test may be presented for a patient. In this example, a first laboratory may perform the first test, a second laboratory may perform the second test, and a third laboratory may perform both the first and the second test. In this example, information may be presented, and a decision may be made by a health care provider that the third laboratory should complete the first and second laboratory tests for this order because the third laboratory can perform both tests. In another example, the health care provider may determine that the first laboratory should complete the first laboratory test and that the third laboratory should complete the second laboratory test because of one or more other factors disclosed herein, including, but not limited to, laboratory qualifications, test processing time, health plan benefit information and the like. Furthermore, the second laboratory may not be chosen to complete the first laboratory test because the second laboratory does not perform the first laboratory test.

In one example, one or more labs are determined based on test processing time. For example, two labs may perform a laboratory test ordered for a patient. In this example, however, processing pursuant to a policy may present information that test results received in one week are desirable. The test processing time of one laboratory may allow test results to be received in one week whereas the test processing time of another laboratory suggests that test results will not be received in one week. In on example, the information presented may include test processing times. In a similar fashion, the location of a laboratory may be presented to enable a health care provider to select a laboratory testing facility closer to the health care provider. In another example, multiple laboratories may be presented for a single test. For example, one laboratory facility—such as a physician office laboratory—that is in close proximity to a patient may be presented for collecting a sample from the patient for the laboratory test while another laboratory facility may be presented for sample analysis.

Figure 5:
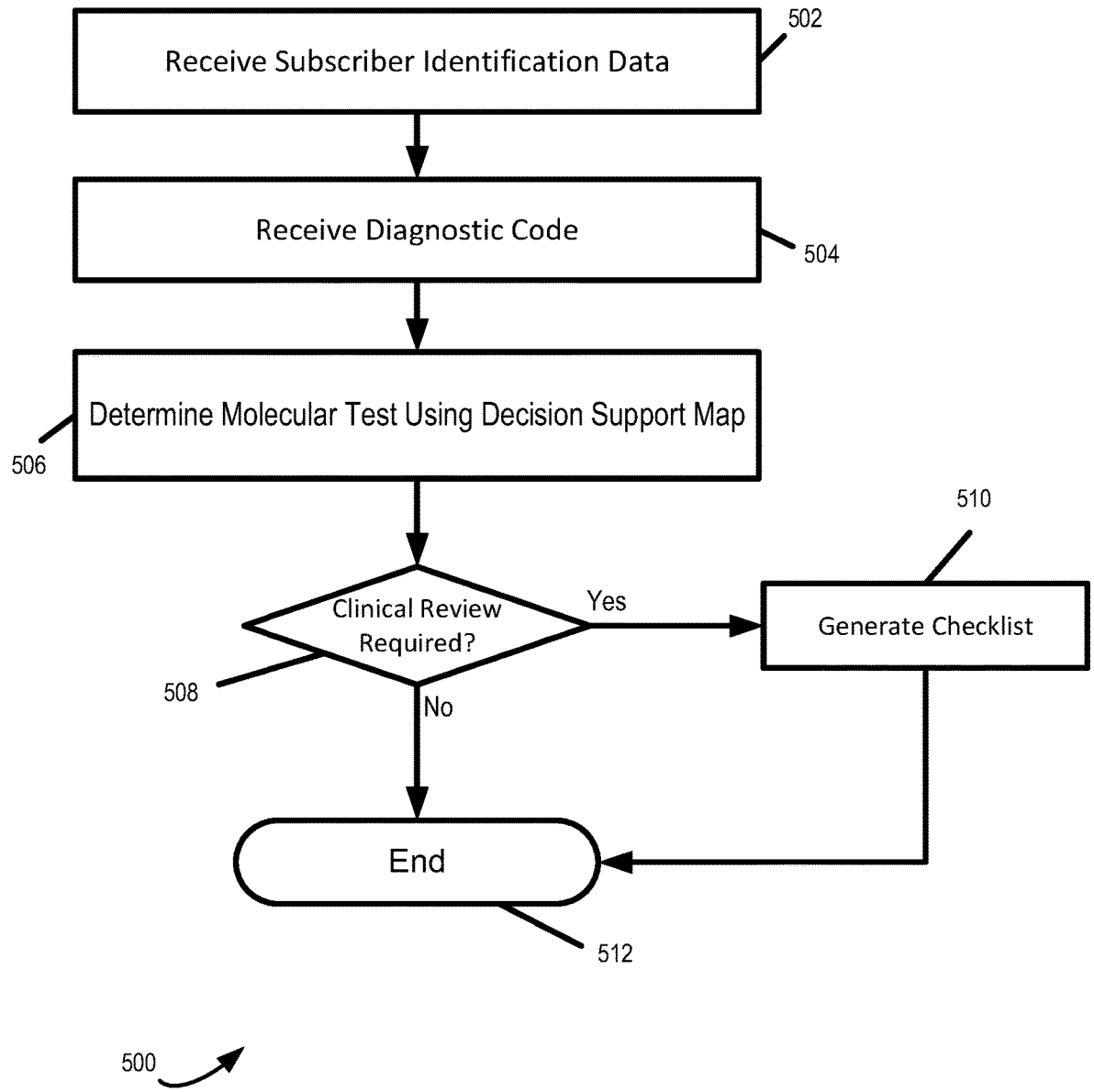
FIG. 5 is a flowchart illustrating an example of a method for providing enhanced decision support according to aspects of the disclosure.

FIG. 5 is a flowchart illustrating an example of a process 500 for providing enhanced decision support. In the process shown, the system first receives subscriber identification data at block 502. A subscriber is a subject that subscribes to a particular insurance plan or health services plan. For example, the user may enter a subscriber number. In another example, the user may search, using for instance the member's first or last name to search for a user and then select the appropriate member. The system then receives a diagnostic code at block 504. In this example, the diagnostic code is associated with a molecular test. In some examples, the user may enter the diagnosis code, a partial code, or a description or partial description of a test in order to identify the particular code to be entered.

Continuing with FIG. 5, the system next determines the molecular test to be ordered for the member at block 506, using the decision support map to map the desired test to a laboratory specific test. A molecular test may be designated as a decision support test and be mapped to particular testing laboratories with particular, laboratory specific names and/ or codes. The system next evaluates the test and the subscriber information to determine whether a clinical review is required at block 508. If a clinical review is required, the system may generate a checklist at block 510. A genetic counselor can be engaged to fill out the checklist in order to allow the molecular test to be ordered by the user and for the appropriate lab to be suggested to the user for selection. The checklist may optionally be transmitted to the generic counselor's or another user's computing device using a network connection. Once the determination of whether a clinical review is required is complete and a checklist generated, the process 500 ends at block 512.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The use of "configured" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific aspects and features thereof, it will be appreciated that those skilled in the art, upon attaining an understanding of the foregoing may readily produce alterations to, variations of, and equivalents. Accordingly, it should be understood that the present disclosure has been presented for purposes of example rather than limitation, and does not preclude inclusion of such modifications, variations and/or additions to the present subject matter.

The invention claimed is:

1. A system comprising:
   a non-transitory computer-readable medium storing computer program code for generating decision support maps; and
   a processing device communicatively coupled to the non-transitory computer-readable medium, wherein the processing device is configured for executing the computer program code to perform operations comprising:
   defining a plurality of decision support tests, a decision support test including stored decision support test data elements configured to identify the decision support test in a centralized laboratory test data management system, wherein the decision support test corresponds to a laboratory test defined differently across a plurality of lab computer systems;
   receiving a directory file from at least one of a plurality of lab computer systems, the directory file including a plurality of test identifiers, at least some of the test identifiers corresponding to molecular tests;
   caching intermediate data corresponding to the stored decision support test data elements and the plurality of test identifiers;
   parsing, using the intermediate data, the directory file to identify a plurality of lab test data elements corresponding to the plurality of test identifiers;
   comparing the lab test data elements for each of the plurality of test identifiers to the stored decision support test data elements to produce a comparison result;
   applying conditional decision support test auto-mapping rules configured for the decision support test to prevent overlap between decision support test mapping rules among the plurality of decision support tests, wherein the auto-mapping rules compare the laboratory test across the plurality of lab computer systems to the decision support test;
   producing, based on the conditional decision support test auto-mapping rules, one or more decision support maps for mapping test identifiers to decision support tests, wherein at least some of the test identifiers and decision support tests correspond to the molecular tests;
   storing the one or more decision support maps for the test identifiers and the decision support tests to facilitate interaction between the plurality of lab computer systems and the centralized laboratory test data management system with respect to the molecular tests;
   accessing a user-defined specification for a horizontal portal, a vertical portal, or a combination horizontal and vertical portal to present decision support tests, laboratories, and policies in one or more portal pages on a diagnostic computing device;
   generating customized information based on the user-defined specification and using the one or more decision support maps, the customized information including at least some of the molecular tests, some of the laboratories, and some of the policies;
   formatting one or more portal pages according to the user-defined specification for the horizontal portal, the vertical portal, or the combination horizontal and vertical portal; and
   electronically providing the customized information to the diagnostic computing device in the one or more portal pages as formatted.

2. The system of claim 1 wherein the operations further comprise:
   receiving a molecular test order from the diagnostic computing device;
   mapping the molecular test order to one of the decision support tests using the one or more decision support maps;
   determining a lab to be used to fulfill the molecular test order based on the mapping and the customized information; and
   electronically sending the molecular test order to the lab.

3. The system of claim 2 wherein the operations further comprise:
receiving identification data for a subject of the molecular test order;
receiving a diagnostic code associated with the molecular test order; and
determining that a review of the molecular test order is required based on at least one of the identification data or the diagnostic code.

4. The system of claim 3 wherein the operations further comprise:
generating a checklist for use by a genetic counselor; and
displaying or transmitting the checklist.

5. The system of claim 1, wherein mappings produced based on the comparison result include definitive mappings and non-definitive mappings, and the operations further comprise:
displaying at least one of definitive mappings or non-definitive mappings to an operator; and
receiving input from the operator to convert the non-definitive mappings to definitive mappings or to alter the definitive mappings prior to storing at least one of the one or more decision support maps.

6. The system of claim 1 wherein the operations further comprise:
receiving new decision support categories; and
selectively updating the one or more decision support maps based on the new decision support categories in response to input from an operator.

7. A method comprising:
defining, by a processing device, a plurality of decision support tests, a decision support test including stored decision support test data elements configured to identify the decision support test in a centralized laboratory test data management system, wherein the decision support test corresponds to a laboratory test defined differently across a plurality of lab computer systems;
receiving, by the processing device, a directory file from at least one of a plurality of lab computer systems, the directory file including a plurality of test identifiers, at least some of the test identifiers corresponding to molecular tests;
caching, by the processing device, intermediate data corresponding to the stored decision support test data elements and the plurality of test identifiers;
parsing, by the processing device using the intermediate data, the directory file to identify a plurality of lab test data elements corresponding to the plurality of test identifiers;
comparing, by the processing device, the lab test data elements for each of the plurality of test identifiers to the stored decision support test data elements to produce a comparison result;
applying, by the processing device, conditional decision support test auto-mapping rules configured for the decision support test to prevent overlap between decision support test mapping rules among the plurality of decision support tests, wherein the auto-mapping rules compare the laboratory test across the plurality of lab computer systems to the decision support test;
producing, by the processing device, based on the conditional decision support test auto-mapping rules, one or more decision support maps for mapping test identifiers to decision support tests, wherein at least some of the test identifiers and decision support tests correspond to the molecular tests;
storing, by the processing device, the one or more decision support maps for the test identifiers and the decision support tests to facilitate interaction between the plurality of lab computer systems and the centralized laboratory test data management system with respect to the molecular tests;
accessing, by the processing device, a user-defined specification for a horizontal portal, a vertical portal, or a combination horizontal and vertical portal to present decision support tests, laboratories, and policies in one or more portal pages on a diagnostic computing device;
generating, by the processing device, customized information based on the user-defined specification and using the one or more decision support maps, the customized information including at least some of the molecular tests, some of the laboratories, and some of the policies;
formatting, by the processing device, one or more portal pages according to the user-defined specification for the horizontal portal, the vertical portal, or the combination horizontal and vertical portal; and
electronically providing the customized information to the diagnostic computing device in the one or more portal pages as formatted.

8. The method of claim 7 further comprising:
receiving a molecular test order from the diagnostic computing device;
mapping the molecular test order to one of the decision support tests using the one or more decision support maps;
determining a lab to be used to fulfill the molecular test order based on the mapping and the customized information; and
electronically sending the molecular test order to the lab.

9. The method of claim 8 further comprising:
receiving identification data for a subject of the molecular test order;
receiving a diagnostic code associated with the molecular test order; and
determining that a review of the molecular test order is required based on at least one of the identification data or the diagnostic code.

10. The method of claim 9 further comprising:
generating a checklist for use by a genetic counselor; and
displaying or transmitting the checklist.

11. The method of claim 7, wherein mappings produced based on the comparison result include definitive mappings and non-definitive mappings, the method further comprising:
displaying at least one of definitive mappings or non-definitive mappings to an operator; and
receiving input from the operator to convert the non-definitive mappings to definitive mappings or to alter the definitive mappings prior to storing at least one of the one or more decision support maps.

12. The method of claim 7 further comprising:
receiving new decision support categories; and
selectively updating the one or more decision support maps based on the new decision support categories in response to input from an operator.

13. A non-transitory computer-readable medium including computer program code executable by a processor to cause the processor to perform operations, the operations comprising:
defining a plurality of decision support tests, a decision support test including stored decision support test data elements configured to identify the decision support test in a centralized laboratory test data management system, wherein the decision support test corresponds to a laboratory test defined differently across a plurality of lab computer systems;

receiving a directory file from at least one of a plurality of lab computer systems, the directory file including a plurality of test identifiers, at least some of the test identifiers corresponding to molecular tests;

caching intermediate data corresponding to the stored decision support test data elements and the plurality of test identifiers;

parsing, using the intermediate data, the directory file to identify a plurality of lab test data elements corresponding to the plurality of test identifiers;

comparing the lab test data elements for each of the plurality of test identifiers to the stored decision support test data elements to produce a comparison result;

applying conditional decision support test auto-mapping rules configured for the decision support test to prevent overlap between decision support test mapping rules among the plurality of decision support tests, wherein the auto-mapping rules compare the laboratory test across the plurality of lab computer systems to the decision support test;

producing, based on the conditional decision support test auto-mapping rules, one or more decision support maps for mapping test identifiers to decision support tests, wherein at least some of the test identifiers and decision support tests correspond to the molecular tests;

storing the one or more decision support maps for the test identifiers and the decision support tests to facilitate interaction between the plurality of lab computer systems and the centralized laboratory test data management system with respect to the molecular tests;

accessing a user-defined specification for a horizontal portal, a vertical portal, or a combination horizontal and vertical portal to present decision support tests, laboratories, and policies in one or more portal pages on a diagnostic computing device;

generating customized information based on the user-defined specification and using the one or more decision support maps, the customized information including at least some of the molecular tests, some of the laboratories, and some of the policies;

formatting one or more portal pages according to the user-defined specification for the horizontal portal, the vertical portal, or the combination horizontal and vertical portal; and electronically providing the customized information to the diagnostic computing device in the one or more portal pages as formatted.

14. The non-transitory computer-readable medium of claim 13 wherein the operations further comprise:
receiving a molecular test order from the diagnostic computing device;
mapping the molecular test order to one of the decision support tests using the one or more decision support maps;
determining a lab to be used to fulfill the molecular test order based on the mapping and the customized information; and
electronically sending the molecular test order to the lab.

15. The non-transitory computer-readable medium of claim 14 wherein the operations further comprise:
receiving identification data for a subject of the molecular test order;
receiving a diagnostic code associated with the molecular test order;
determining that a review of the molecular test order is required based on at least one of the identification data or the diagnostic code;
generating a checklist for use by a genetic counselor; and
displaying or transmitting the checklist.

16. The non-transitory computer-readable medium of claim 13, wherein mappings produced based on the comparison result include definitive mappings and non-definitive mappings, and the operations further comprise:
displaying at least one of definitive mappings or non-definitive mappings to an operator; and
receiving input from the operator to convert the non-definitive mappings to definitive mappings or to alter the definitive mappings prior to storing at least one of the one or more decision support maps.

17. The non-transitory computer-readable medium of claim 13 wherein the operations further comprise:
receiving new decision support categories; and
selectively updating the one or more decision support maps based on the new decision support categories in response to input from an operator.

* * * * *